(12) United States Patent
Yokokawa et al.

(10) Patent No.: US 6,605,741 B2
(45) Date of Patent: Aug. 12, 2003

(54) SYNTHETIC METHOD OF α-KETOL UNSATURATED FATTY ACIDS

(75) Inventors: Yoshihiro Yokokawa, Yokohama (JP); Koji Kobayashi, Yokohama (JP); Shosuke Yamamura, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 10/110,239

(22) PCT Filed: Jan. 31, 2001

(86) PCT No.: PCT/JP01/00660
§ 371 (c)(1),
(2), (4) Date: Apr. 10, 2002

(87) PCT Pub. No.: WO02/060850
PCT Pub. Date: Aug. 8, 2002

(65) Prior Publication Data
US 2002/0156304 A1 Oct. 24, 2002

(51) Int. Cl.$^7$ .............................................. C07L 321/00
(52) U.S. Cl. ....................................... 562/577; 562/587
(58) Field of Search .................................. 562/577, 587

(56) References Cited

U.S. PATENT DOCUMENTS

| | | |
|---|---|---|
| 4,188,374 A | 2/1980 | Voerman et al. |
| 6,057,157 A | 5/2000 | Yokoyama et al. |

FOREIGN PATENT DOCUMENTS

| | | |
|---|---|---|
| EP | 0 823 994 A1 | 2/1998 |
| JP | 53-034926 A2 | 3/1978 |
| JP | 9-295908 A2 | 11/1997 |
| JP | 11-029410 A | 2/1999 |
| WO | WO 97/32478 A | 12/1997 |

OTHER PUBLICATIONS

Gunstone, F.D. et al Chemistry and Physics of Lipids (1975), 15(2) 174–88.*
Ruder, S.; Improved Method for Samarium Diiodide Induced Reductive Coupling Reactions of Acid Halides; Tetrahedron Letters., Pergamen Press Ltd., 1992, vol. 33, No. 19, p. 2621–2624.
Narny, J. et al.; Samarium Diiodide in Tetrahydropyran: Preparation and some Reactions in Organic Chemistry; Tetrahedron Letters., Elsevier Science Ltd., 1994 vol. 35, No. 11, p. 1723–1726.
Corey, E.J. et al.; Application of Bisthio Carbanions to the Elaboration of 2–Cyclohexenone Systems; The Journal of Organic Chemistry, 1968, vol. 33, No. 11, p. 298–300.
Brown, C. et al.; Induced Conjugate Addition of Simple 2–Lithio–1,3–dithians to Cyclic α,β–Unsaturated Ketones; J.C.S. Chem. Comm., 1979, p. 100–101.
Ogura, K. et al., A Versatile Reacent for Synthesis of α–Hydroxy Aldehydes and Ketones—Methylthiomethyl p–Tolyl Sulfone; Tetrahedron Letters, Pergemon Press Ltd., 1986, vol. 27, No. 31, p. 3665–3668.

Ogura, K. et al.; A Novel Route From A Carboxylic Acid To A Carbaldehyde Using Methylthtomethyl; Tetrahedron Letters, Pergemon Press Ltd., 1983, vol. 24, No. 51, p. 5761–5762.

Gunstone, F.D. et al.; Fatty Acids Part 47* The Mass Spectra Of Bis(Trimethylsilyloxy) and Methoxy Trimethylsilyloxy Ethers Derived From a Series of Methyl Epoxyoctadecenoates and Methyl Epoxyoctadecynoates; Chemistry and Physics of Lipids, 1975, vol. 15, No. 2, p. 198–208.

Leblanc, Y. et al.; Synthesis of 5–O–Benzoyl–14,15–didehydroleukotriene $B_4$ ($LTB_4$) Ethyl Ester and 5–0–Benzoyl–14,15–didehydro–20–hydroxylleukotriene $B_4$ ($LTB_4$) Ethyl Ester: Direct Precursors of Labeled $LTB_{4S}$; The Journal of Organic Chemistry, 1988, vol. 53, No. 2, p. 265–267.

Zhang, Z. et al., A facile synthetic method for chiral 1,2–epoxides and the total synthesis of chiral pheromone epoxides; Tetrahedron: Asymmetry, 1999, vol. 10, p. 837–840.

* cited by examiner

Primary Examiner—Paul J. Killos
(74) Attorney, Agent, or Firm—Venable LLP; Fei-Fei Chao

(57) ABSTRACT

The present invention provides an efficient synthetic method of α-ketol unsaturated fatty acid having a double bond at a β-position to the ketone group thereof. It comprises the steps of: preparing compound (4) by reacting monosubstituted acetylene (2) with epoxide (3); and preparing α-ketol unsaturated fatty acid (1) from said compound (4) as shown in Reaction Formula 1:

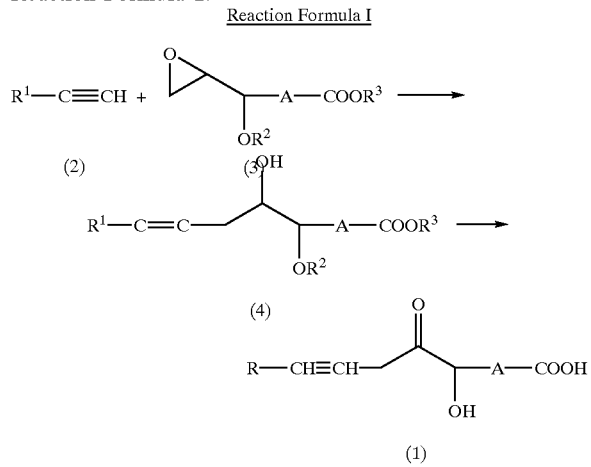

wherein $R^1$ represents an alkyl group of 1–18 carbon atoms or an aliphatic hydrocarbon group of 2–18 carbon atoms having 1–5 double or triple bonds at given positions; $R^2$ represents a protecting group for a hydroxyl group; $R^3$ represents a protecting group for a carboxyl group; R is identical to $R^1$ or, when $R^1$ has one or more triple bonds, represents an aliphatic hydrocarbon group in which each triple bond of $R^1$ is converted to a double bond; and A represents an alkylene group of 1–18 carbon atoms.

14 Claims, No Drawings

SYNTHETIC METHOD OF α-KETOL UNSATURATED FATTY ACIDS

FIELD OF THE INVENTION

This invention relates to a synthetic method of an α-ketol unsaturated fatty acid and, in particular, to improve the yield in a synthesis of an α-ketol unsaturated fatty acid having a double bond at a β-position to the ketone group thereof.

BACKGROUND OF THE INVENTION

Heretofore, various actions of ketol fatty acids have been known in the art, and in recent years it has been reported that some of ketol fatty acids have a flower bud formation inducing effect (Japanese Unexamined Patent Publication Nos. 9-295908 and 11-29410).

Several attempts have been made for preparing ketol fatty acids efficiently. As in the case of α-ketol unsaturated fatty acid (1) represented below, however, due to a double bond existing at a β-position to the ketone group there is a problem that it is hard to be efficiently prepared by organic synthetic methods.

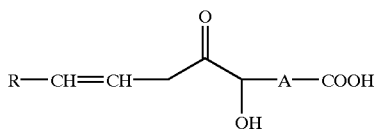

(1)

As for examples of synthetic methods of α-ketols, the following Reaction Formulae I to III may be provided.

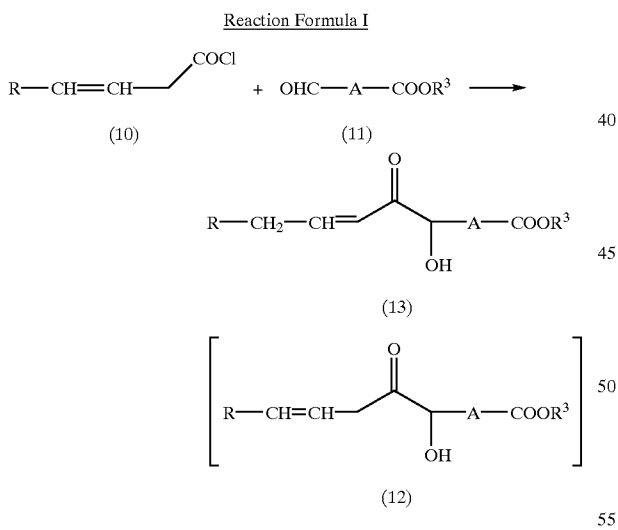

Reaction Formula I

The Reaction Formula I shows a method to provide α-ketol (12) by condensing acid chloride (10) and aldehyde (11) in the presence of samarium iodide (Tetrahedron Letters, Vol. 33, No. 19, 2621–2624 (1992), and Tetrahedron Letters, Vol. 35. No. 11, 1723–1726 (1994)). However, Reaction Formula I provided only a complicated mixture as a resulting product. Furthermore, the purification of such a product only gave compound (13) in which the double bond of α-ketol (12) was transferred at low yield, so that Reaction Formula I could not allow the isolation of desired α-ketol (12).

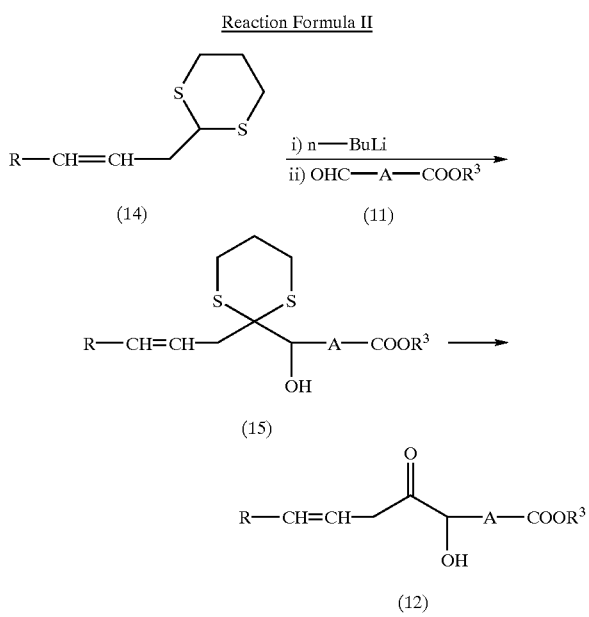

The Reaction Formula II shows a method that dithiane (14) is converted into its lithio-derivative by a lithiation process using alkyl lithium such as n-butyllithium and then the lithio-derivative is condensed with aldehyde (11) to provide compound (15), followed by converting a dithio part of compound (15) into a carbonyl group to obtain an α-ketol (12) (J. Org. Chem., Vol. 33, No. 1, 298–300 (1968), and J. C. S. Chem. Comm., 100–101 (1979)). In this case, however, the resultant was also a complicated mixture, so that the target compound could not be isolated therefrom.

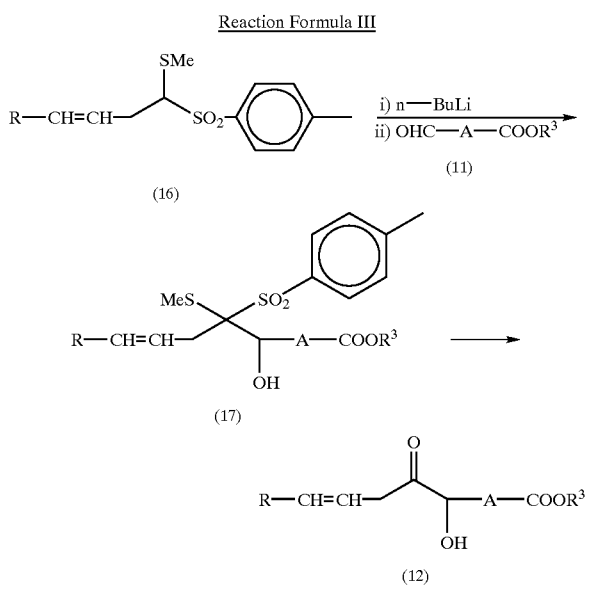

The Reaction Formula III shows a method using methylthiomethyl p-tolylsulfone derivative (16) which anions may present more stable than those of the dithiane. Namely, the methylthiomethyl p-tolylsulfone derivative (16) is reacted with aldehyde (11) just as in the case of Reaction Formula II to provide compound (17), followed by converting a thiomethylsulfone part of compound (17) into a carbonyl group to obtain α-ketol (12) (Tetrahedron Letters, Vol. 27, No. 31, 3665–3668 (1986), and Tetrahedron Letters, Vol. 24, No. 51, 5761–5762 (1983)). In this method, compound (17) could be isolated but the yield was extremely low as 20% or less. Also, subsequent conversion reaction to a ketone gave a complicated mixture, so that the isolation was extremely difficult.

Thus, in the case of α-ketol unsaturated fatty acid in which a double bond is present at a β-position to the ketone, the yield of its skeleton-forming reaction is extremely low as the double bond may be easily transferred. This is the reason why it is hard to obtain the desired α-ketol unsaturated fatty acid efficiently.

SUMMARY OF THE INVENTION

The present invention has been accomplished in view of the above problems of the prior art. It is, therefore, a object of this invention to provide a method for efficiently synthesizing α-ketol unsaturated fatty acid having a double bond at a β-position to the ketone.

As a result of the diligent studies conducted by the inventors for attaining the above object, it has be found that by a reaction between a monosubstituted acetylene and an epoxide a carbon skeleton of α-ketol unsaturated fatty acid can be formed efficiently. Thus, the present invention has been accomplished.

Namely, a method of synthesizing an α-ketol unsaturated fatty acid in accordance with the present invention comprises the steps of:
preparing compound (4) by reacting monosubstituted acetylene (2) with epoxide (3); and
preparing α-ketol unsaturated fatty acid (1) from said compound (4), as shown in the following Reaction Formula 1:

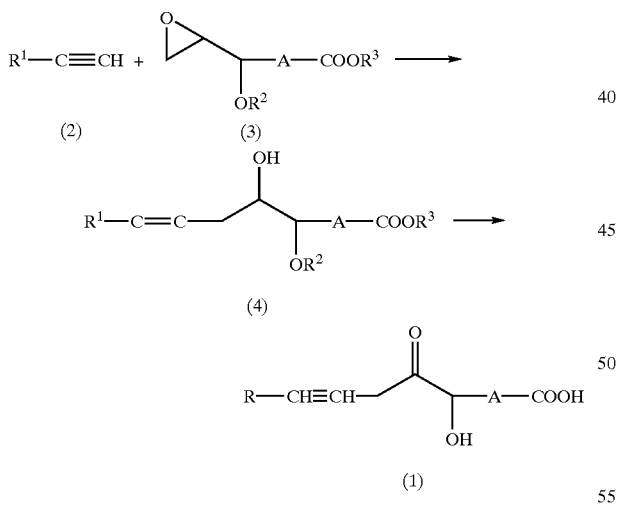

wherein
R$^1$ represents an alkyl group of 1–18 carbon atoms or an aliphatic hydrocarbon group of 2–18 carbon atoms having 1–5 double or triple bonds at given positions;
R$^2$ represents a protecting group for a hydroxyl group;
R$^3$ represents a protecting group for a carboxyl group;
R is identical to R$^1$ or, when R$^1$ has one or more triple bonds, R represents an aliphatic hydrocarbon group in which each triple bond of R$^1$ is converted to a double bond; and A represents an alkylene group of 1–18 carbon atoms.
The method of the present invention preferably comprises the steps of:
reducing said compound (4) to produce compound (5);
oxidizing a hydroxyl group of said compound (5) to produce compound (6); and
deprotecting R$^2$ and R$^3$ of said compound (6) to produce said α-ketol unsaturated fatty acid (1), as shown in Reaction Formula 2:

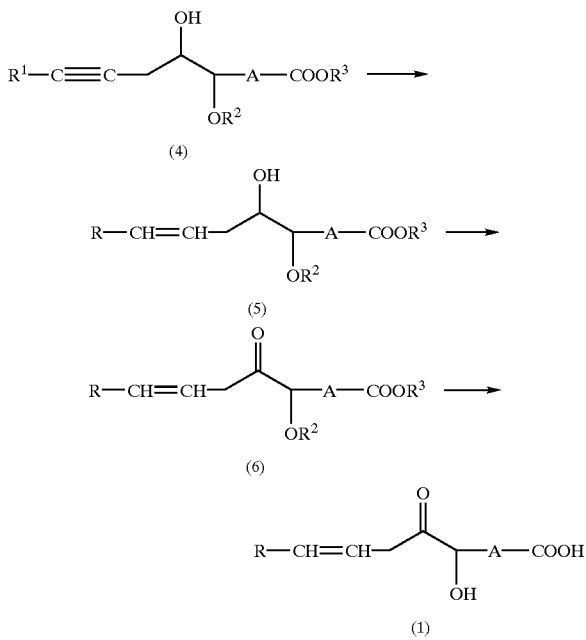

wherein R$^1$, R$^2$, R$^3$, R, and A are the same as defined in said Reaction Formula 1.

Also, the method of the present invention preferably comprises the steps of:
reducing said compound (4) to produce compound (5);
deprotecting R$^3$ of said compound (5) to produce compound (7);
oxidizing a hydroxyl group of said compound (7) to produce compound (8); and
deprotecting R$^2$ of said compound (8) to produce said α-ketol unsaturated fatty acid (1), as shown in Reaction Formula 3:

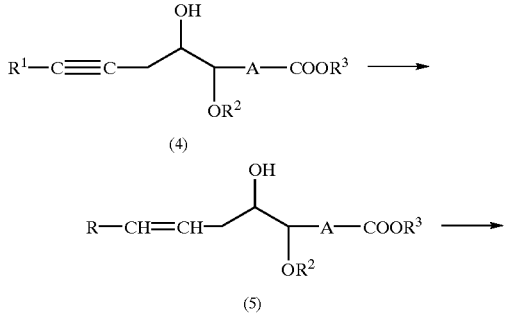

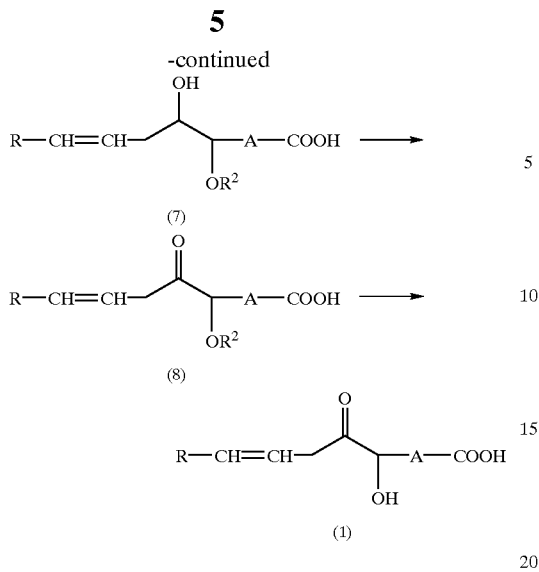

(7)

(8)

(1)

wherein $R^1$, $R^2$, $R^3$, R, and A are the same as defined in said Reaction Formula 1.

In the present invention, $R^1$ preferably represents $R^4$—C≡C—$CH_2$—, where $R^4$ represents an alkyl group of 1–7 carbon atoms.

$R^4$ preferably represents ethyl group.

"A" preferably represents an alkylene group expressed by —$(CH_2)n$—, where n is an integer of 1 to 10.

"n" is preferably 7.

$R^2$ preferably represents an ether-type protecting group.

The double bond of α-ketol unsaturated fatty acid (1) preferably has a cis-configuration.

An intermediate for synthesis of α-ketol unsaturated fatty acid (1) in accordance with the present invention is represented by the general formula (4):

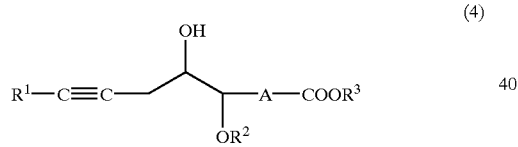

(4)

wherein $R^1$ represents an alkyl group of 1–18 carbon atoms or an aliphatic hydrocarbon group of 2–18 carbon atoms having 1–5 double or triple bonds at given positions;

$R^2$ represents a protecting group for a hydroxyl group;

$R^3$ represents a protecting group for a carboxyl group; and

A represents an alkylene group of 1–18 carbon atoms.

In a method of synthesizing an optically active α-ketol unsaturated fatty acid in accordance with the present invention, it is preferably that in any methods mentioned above an asymmetric carbon atom of —C($OR^2$)— in said epoxide (3) has either of R-configuration or S-configuration and that an asymmetric carbon atom in the α-ketol structure of α-ketol unsaturated fatty acid (1) has either of R-configuration or S-configuration.

Also, the method preferably comprises the steps of:

preparing compound (4A) by reacting said monosubstituted acetylene (2) with (R)-epoxide (3A) obtained from compound (21A) which asymmetric carbon atom at an aryl position has R-configuration; and preparing (R)-α-ketol unsaturated fatty acid (1A) from said compound (4A), as shown in the following Reaction Formula 1A:

Reaction Formula 1A

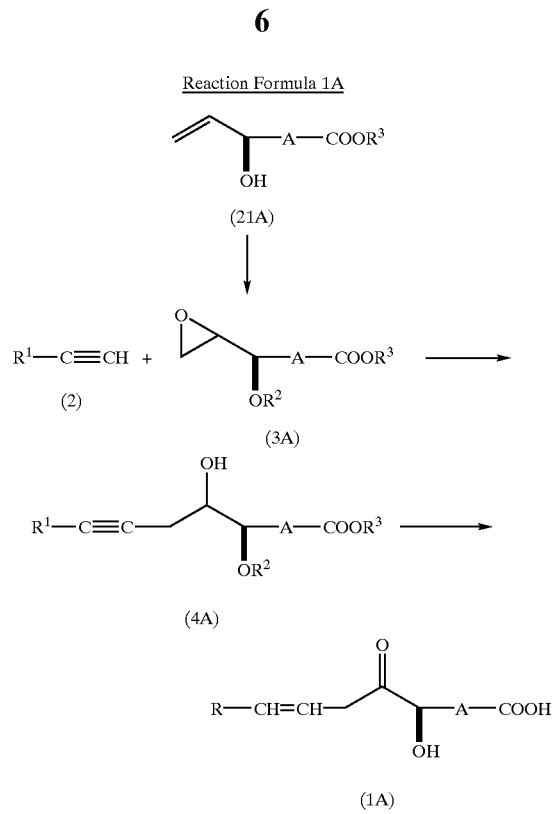

(21A)

(3A)

(4A)

(1A)

wherein $R^1$, $R^2$, $R^3$, R, and A are the same as defined in said Reaction Formula 1.

Also, the method preferably comprises the steps of:

preparing compound (4B) by reacting said monosubstituted acetylene (2) with (S)-epoxide (3B) obtained from compound (21B) which asymmetric carbon atom at an aryl position has S-configuration; and preparing (S)-α-ketol unsaturated fatty acid (1B) from said compound (4B), as shown in the following Reaction Formula 1B:

Reaction Formula 1B

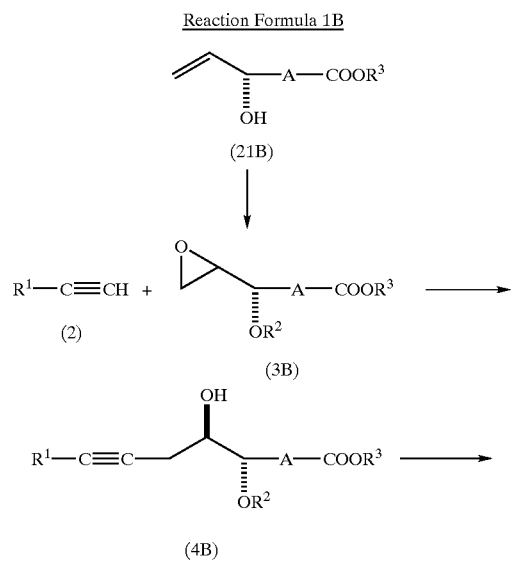

(21B)

(3B)

(4B)

-continued

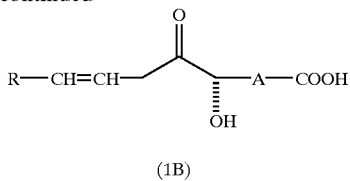

(1B)

wherein $R^1$, $R^2$, $R^3$, R, and A are the same as defined in said Reaction Formula 1.

An optically active intermediate for synthesis of said α-ketol unsaturated fatty acid (1A) or (1B) is represented by the general formula (4A) or (4B):

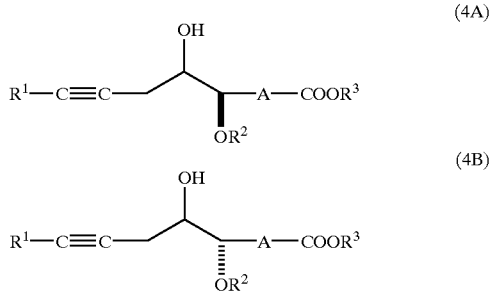

wherein
- $R^1$ represents an alkyl group of 1–18 carbon atoms or an aliphatic hydrocarbon group of 2–18 carbon atoms having 1–5 double or triple bonds at given positions;
- $R^2$ represents a protecting group for a hydroxyl group;
- $R^3$ represents a protecting group for a carboxyl group; and
- A represents an alkylene group of 1–18 carbon atoms.

BEST MODES FOR CARRYING OUT THE INVENTION

In Reaction Formula 1, $R^1$ of monosubstituted acetylene (2) represents an alkyl group of 1–18 carbon atoms or an aliphatic hydrocarbon group of 2–18 carbon atoms having 1–5 double or triple bonds at optional positions therein.

The alkyl group may be either of a straight or a branched chain. Examples thereof include methyl, ethyl, propyl, butyl, pentyl, isopropyl, tert-butyl, hexyl, octyl, decyl, tetradecyl, octadecyl, 1-methylpropyl, 1-ethylpropyl, 3-methylbutyl, and 2-ethylhexyl. Preferably, the alkyl group has 1–10 carbon atoms.

The aliphatic hydrocarbon group having double or triple bonds may be either of a straight or a branched chain, where these multiple bonds do not limited to specific positions. The aliphatic hydrocarbon group has preferably 1–10 carbon atoms including one triple bond, and more preferably a group represented by $R^4$—C≡C—$CH_2$—. $R^4$ represents an alkyl group of 1–7 carbon atoms, and preferably ethyl group.

A protecting group $R^2$ for a hydroxyl group and another protecting group $R^3$ for a carboxyl group in epoxide (3) are not limited, unless any trouble is caused in the synthetic method of the present invention. Examples of the protecting group $R^2$ include ether-type protecting groups such as methoxymethyl (MOM), 2-methoxyethoxymethyl (MEM), tetrahydropyranyl (THP), 1-ethoxyethyl, tert-butyl, benzyl, trimethylsilyl (TMS), and tert-butyldimethylsilyl (TBDMS); ester-type protecting groups such as formyl, acetyl, and benzoyl; carbamate-type protecting groups such as benzyloxycarbonyl; and sulfonyl-type protecting groups such as p-toluenesulfonyl. Among them, it is preferably the ether-type protecting group, and more preferably MOM, MEM or TBDMS.

As for the protecting group $R^3$, for example, methyl, ethyl, tert-butyl, benzyl, methoxymethyl (MOM), 2-methoxyethoxymethyl (MEM), or tetrahydropyranyl (THP) can be used.

In Reaction Formula 1, "A" represents a straight or branched alkylene group of 1–18 carbon atoms, preferably a straight alkylene group of 1–10 carbon atoms, and more preferably —$(CH_2)_7$—.

According to the synthetic method of the present invention, compound (4) is prepared as an intermediate by reacting monosubstituted acetylene (2) with epoxide (3), and then desired α-ketol unsaturated fatty acid (1) is obtained from compound (4). "R" of α-ketol unsaturated fatty acid (1) is derived from $R^1$ of monosubstituted acetylene (2) used as a starting material. R may be identical to $R^1$ or, if $R^1$ has one or more triple bonds, an aliphatic hydrocarbon group in which such triple bonds are converted into double bonds.

In the present invention, unless otherwise specified, $R^1$, $R^2$, $R^3$, $R^3$, R, A, and n are defined as described above.

Although each double bond in α-ketol unsaturated fatty acid (1) may be either of cis- or trans-configuration, in view of a effect such as a flower bud formation inducing effect or the like, a cis-configuration is preferable. Also, there is at least one asymmetric carbon atom in α-ketol unsaturated fatty acid (1) of the present invention. The present invention includes each of optical isomers depend on the asymmetric carbon atom and a mixture thereof. In each synthetic step of the present invention, using well-known methods an optical resolution can be effected.

In Reaction Formula 1, the reaction between monosubstituted acetylene (2) and epoxide (3) can be performed by converting the monosubstituted acetylene (2) into its 1-lithio derivative with an organic lithium compound such as n-butyllithium or phenyllithium, and then by reacting the derivative with epoxide (3). If required, a Lewis acid such as boron trifluoride etherate or a base such as ethylenediamine or tetramethylethylenediamine may be added thereto. As for a solvent, tetrahydrofuran (THF), diethyl ether, dimethyl sulfoxide (DMSO), or the like can be used. The reaction is preferably performed at a low temperature of –50° C. or less.

In Reaction Formula 1, the reaction for converting compound (4) into α-ketol unsaturated fatty acid (1) includes reduction of triple bonds to double bonds, oxidation of a hydroxyl group, and deprotection of $R^2$ and $R^3$ in appropriate order. For example, As shown in Reaction Formula 2, after the reduction of triple bonds to double bonds, the oxidation of a hydroxyl group and the deprotection of $R^2$ and $R^3$ are performed successively. The order of deprotection of $R^2$ and $R^3$ is not limited and both $R^2$ and $R^3$ may be removed by deprotection at the same time depending on the species thereof. Also, as shown in Reaction Formula 3, it is possible to perform reduction of triple bonds to double bonds, the deprotection of carboxyl-protecting group $R^3$, the oxidation of a hydroxyl group, and the deprotection of $R^2$ in this order. However, Reaction Formula 2 is preferable.

For the reduction of compound (4), a selective reduction process should be selected depending on a cis- or trans-configuration of each double bond to be obtained. For example, a selective reduction from triple bonds to cis-double bonds can be performed by a catalytic reduction process using nickel acetate-$NaBH_4$ as a catalyst or another catalytic reduction process using Pd-$CaCO_3$ or Pd-$BaSO_4$ as a catalyst in the presence of lead acetate or quinoline. As for a solvent to be used, alcohols such as methanol and ethanol, ethyl acetate, acetic acid, diethyl ether, benzene, hexane, dioxane, and the like can be used. The reaction temperature may be in the range of room temperature to a reflux temperature. Also, the above goal can be achieved by performing a hydroboration process with diborane to produce a corresponding vinyl borane derivative and then hydrolyzing the derivative with acetic acid or the like. Furthermore, it can be achieved by a reduction process heating a material in methanol together with a zinc-copper alloy.

A selective reduction to trans-double bonds includes a process using an alkali metal such as sodium, lithium, or potassium in an amine solvent such as liquid ammonia, methylamine, ethylamine, or ethylenediamine. As for a solvent in this case, in addition to the amine described above, an alcohol, diethyl ether, THF, dimethoxyethane (DME), and the like can be used.

Any reaction for forming a carbonyl group of α-ketol in conversion from compound (5) into compound (6) or from compound (7) into compound (8) can be performed by an oxidation of a hydroxyl group. Such oxidation may be chromic acid oxidation, DMSO oxidation, or an oxidation using dimethyl sulfide (DMS)/N-chlorosuccinimide (NCS), o-iodoxybenzoic acid, or the like.

In the chromic acid oxidation, chromic compounds including chlomium oxide (VI), a dichromate such as potassium dichromate or sodium dichromate, pyridinium chlorochromate (PCC), pyridinium dichromate (PDC), or pyridinium fluorochromate (PFC) can be used. In the case using chromium oxide (VI) or a dichromate, for example, under an acidic condition with sulfuric acid the reaction can be carried out in a solvent such as acetone, acetic acid, THF, dioxane, diethyl ether, benzene, chlorobenzene, or carbon tetrachloride. Also, there is an another method using chrome oxide (VI)-pyridine complex in a solvent such as pyridine or dichloromethane. In the case using a chrome compound such as PCC, PDC, or PFC, the reaction can be carried out in a solvent such as dichloromethane. In any event, the reaction temperature is typically in the range of 0 to 60° C.

In the DMSO oxidation, the reaction is typically carried out in the presence of an appropriate electrophilic reagent. Depending on a kind of the electrophilic reagent used, it can be broadly classified as DMSO-dicyclohexylcarbodiimide (DCC) method, DMSO-acetic anhydride method, DMSO-phosphorus pentoxide method, DMSO-sulfur trioxide-pyridine method, and so on. In the case of DMSO-DCC method, for example, additionally using pyridine-trifluoroacetic acid is used as a hydrogen donor, the reaction can be carried out in a solvent such as benzene if required. The DMSO-acetic anhydride method is generally carried out without any solvent. The DMSO-phosphorus pentoxide method is carried out in a solvent such as dimethylformamide (DMF). The DMSO-sulfur trioxide-pyridine method is carried out in the presence of trimethylamine. In each of the cases, typically, the reaction temperature may be in the range of room temperature to 70° C.

In the DMS/NCS oxidation, it is preferable that a DMS-NCS complex is prepared in toluene at 0° C. and then subjected to the oxidation process at 0° C. to −25° C.

In the oxidation using o-iodoxybenzoic acid, a solvent may be DMSO, a halogenated hydrocarbon such as chloroform or dichloromethane, an aromatic hydrocarbon such as benzene, xylene, or toluene. The reaction temperature is typically in the range of room temperature to a reflux temperature.

A deprotecting reaction of $R^2$ to be required for obtaining α-ketol unsaturated fatty acid (1) as a final product can be performed by well known methods such as described in "Protective groups in Organic Synthesis", T. W. Greene, and P. G. M. Wuts, John Wiley & Sons, Inc., and so on, depending on a selection of the protecting group. If $R^2$ is TBDMS, for example, the deprotecting reaction can be carried out in a solvent such as acetonitrile, or water with hydrogen fluoride.

The deprotection of $R^3$ also can be performed by well known methods, depending on a selection of the protecting group. In the case where $R^3$ is an alkyl group such as methyl group, for example, the deprotection can be performed by a hydrolysis using a base such as potassium hydroxide or a sodium hydroxide in a solvent such as methanol or water. In addition, it is possible to perform the deprotection with an enzyme such as a lipase.

In each of the conventional methods represented by the respective Reaction Formulae I to III as described above, a carbon skeleton of α-ketol unsaturated fatty acid (1) is formed by a condensation reaction between a carbon of a carbonyl group and a carbon of C—OH group. In the synthetic method of the present invention, on the other hand, an epoxide (3) having a 1,2-epoxy-3-hydroxy structure as a precursor of α-ketol is reacted with monosubstituted acetylene (2) to form a carbon skeleton of α-ketol unsaturated fatty acid. According to the present invention, compound (4) to be an intermediate can be obtained in a high yield of 85% or more and following steps are convenient, so that α-ketol unsaturated fatty acid (1) can be efficiently prepared as a final product.

The monosubstituted acetylene (2) of Reaction Formula 1 can be commercially available or prepared by a well known reaction process. For instance, 1,4-heptadiyne can be prepared by reacting 1-butyne with ethyl magnesium bromide to produce a corresponding magnesium acetylide and then reacting the latter with 3-bromopropane-1-yne (e.g., Japanese Unexamined Patent Publication No. 53-34926, and J. Chem. Ecol., 4, 531–542 (1978)). Another monosubstituted acetylene can be prepared in the same way. Furthermore, it can be prepared by a dehydrohalogenation reaction of 1,2-dihalogenoalkane or halogenoalkene with a base, or a dehlogenation reaction of tetrahalogenoalkane or dihalogenoalkene.

The epoxide (3) can be also prepared by a well known reaction. A representative synthetic example will be shown bellow.

Reaction Formula 4

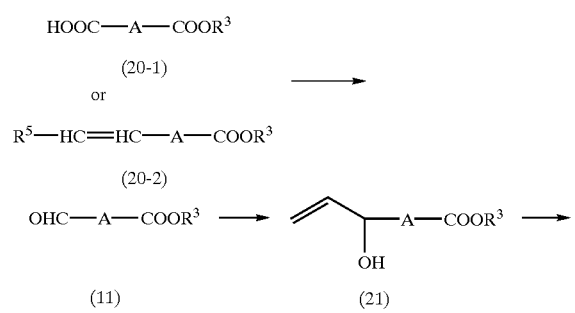

-continued

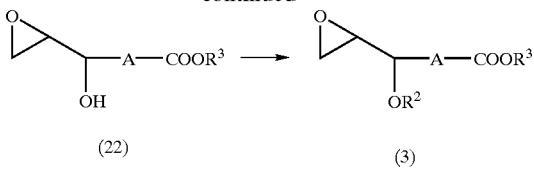

(22) (3)

In Reaction Formula 4, the epoxide (3) can be obtained by: preparing an aldehyde (11) by a selective reduction of dicarboxylic acid halfester (20-1) or by a reductive ozonolysis or a periodate degradation of compound (20-2); converting a formyl group of aldehyde (11) into a $H_2C=CH—CH(OH)—$ group; performing an epoxidation of a double bond; and then protecting a hydroxyl group. Although $R^5$ of compound (20-2) may be any substituent unless otherwise effected on the reaction, it is preferably an alkyl group.

The aldehyde (11) of Reaction Formula 4 can be obtained by each of several methods. For example, the aldehyde (11) may be obtained by reacting dicarboxylic acid halfester (20-1) with 1,1-carbonyldiimidazol to obtain an acid imidazolide and then reducing the latter with lithium aluminium hydride tri-tert-butoxide. These reactions can be typically performed in an anhydrous solvent such as diethylether or THF at a temperature in the range of 0° C. to a reflux temperature.

Alternatively, aldehyde (11) can be obtained by reacting compound (20-2) with ozone to obtain an ozonide and then reducing the latter with dimethylsulfide or the like. This reaction can be typically performed in an organic solvent such as methanol at a temperature in the range of −80° C. to 0° C. As another method, furthermore, aldehyde (11) can be obtained by epoxidation of compound (20-2) with a peracid such as m-chloroperbenzoic acid and then reacting the resulting epoxide with a periodic acid. The epoxidation is typically performed in an organic solvent such as dichloromethane, hexane, ethyl acetate, diethylether, or methanol at a temperature in the range of 0° C. to a reflux temperature. The reaction with the periodic acid is typically performed in an aqueous organic solvent such as a mixture of dioxane with water at a temperature in the range of 0° C. to a reflux temperature.

In a second stage, for example, by Grignard reaction using vinyl magnesium bromide aldehyde (11) can be converted into compound (21). This reaction is typically performed in an anhydrous solvent such as diethylether or THF at a low temperature of −30° C. or less.

In a third stage, for example, compound (21) can be converted into compound (22) by epoxidation with a peracid. The peracid may be perbenzoic acid, m-chloroperbenzoic acid, peracetic acid, hydrogen peroxide, or the like. The solvent may be selected from hydrocarbons such as benzene and hexane, halogenated hydrocarbons such as dichloromethane and chloroform, esters such as ethyl acetate, ethers such as diethyl ether and THF, alcohols such as methanol, and so on. The reaction temperature is typically in the range of 0° C. to a reflux temperature.

In a fourth stage, by protecting a hydroxyl group of compound (22) a desired epoxide (3) can be obtained. The protecting reaction can be performed in a conventional manner depending on a selection of the protecting group (e.g., "Protecting groups in Organic Synthesis" described above). If the protecting group is TBDMS or TMS, for example, the corresponding chlorosilane compound is used for the reaction in the presence of a base such as pyridine, triethylamine, triethanolamine, urea, DBU, or imidazole. The reaction is typically performed in a solvent such as benzene or DMF at a temperature in the range of room temperature to a reflux temperature.

The optical isomer (1A) or (1B), in which the asymmetric carbon atom of α-ketol structure —COC(OH)— in α-ketol unsaturated fatty acid (1) has R- or S-configuration respectively, can be obtained by optical resolution of α-ketol unsaturated fatty acid (1) prepared in the above Reaction Formula 1. Alternatively, as shown in Reaction Formula 1A or 1B, it can be synthesized by a reaction according to Reaction Formulae 1 to 3 using an optically active epoxide (3A) or (3B). The epoxide (3A) or (3B) is an optical isomer in which the carbon at 3-position of 1,2-epoxide-3-hydroxy structure being a precursor of α-ketol structure has R- or S-configuration. The epoxide (3A) or (3B) can be synthesized using a well known reaction. For example, according to the third to fourth stages of the above Reaction Formula 4, it can be prepared from an optically active compound (21A) or (21B) in which an asymmetric carbon atom of —C(OH)— is a R- or S-configuration.

The compound (21A) or (21B) can be obtained from racemic compound (21) thereof by a well known method. For example, a direct optical resolution, which may be performed by a liquid chromatography using an optically active column, can be used. Also, a method including: binding the compound (21) with an optically active compound by an ester bond or the like to induce compound (21) to a diastereomer; separating the diastereomer by a well known process such as recrystallization, thin-layer chromatography, or liquid chromatography; and then breaking the bond can be used. Furthermore, one of optical isomers (21A) and (21B) is reacted by an optically selective enzymatic reaction to compound (21) and is removed as a reaction product, thereby obtaining the other optical isomer.

As a representative example, the racemic compound (21) is selectively reacted with a vinyl acetate using an enzyme such as a lipase to acetylate either the optical isomer (21A) or (21B), and then a separation between a resulting acetylated isomer and an unacetylated isomer is carried out, thereby obtaining an optical isomer (21A) or (21B). The present reaction is typically performed in an organic solvent such as pentane or diisopropyl ether at a temperature in the range of −40° C. to 40° C.

Also, the isomer (21A) or (21B) can be obtained by a deacetylation of the acetylated isomer using a well known method. For example, there are methods for removing an acetyl group by an enzyme such as esterase or lipase, or by treatment with a base such as sodium hydroxide or potassium hydroxide. In this case, if a protecting group $R^3$ for a carboxylic acid at an end of the compound (21A) or (21B) is removed, the carboxyl group may be protected by an appropriate protecting group $R^3$ such as methyl group to obtain the compound (21A) or (21B).

Hereinafter, but not limited to, the present invention will be described by examples.

Reaction Formula 5

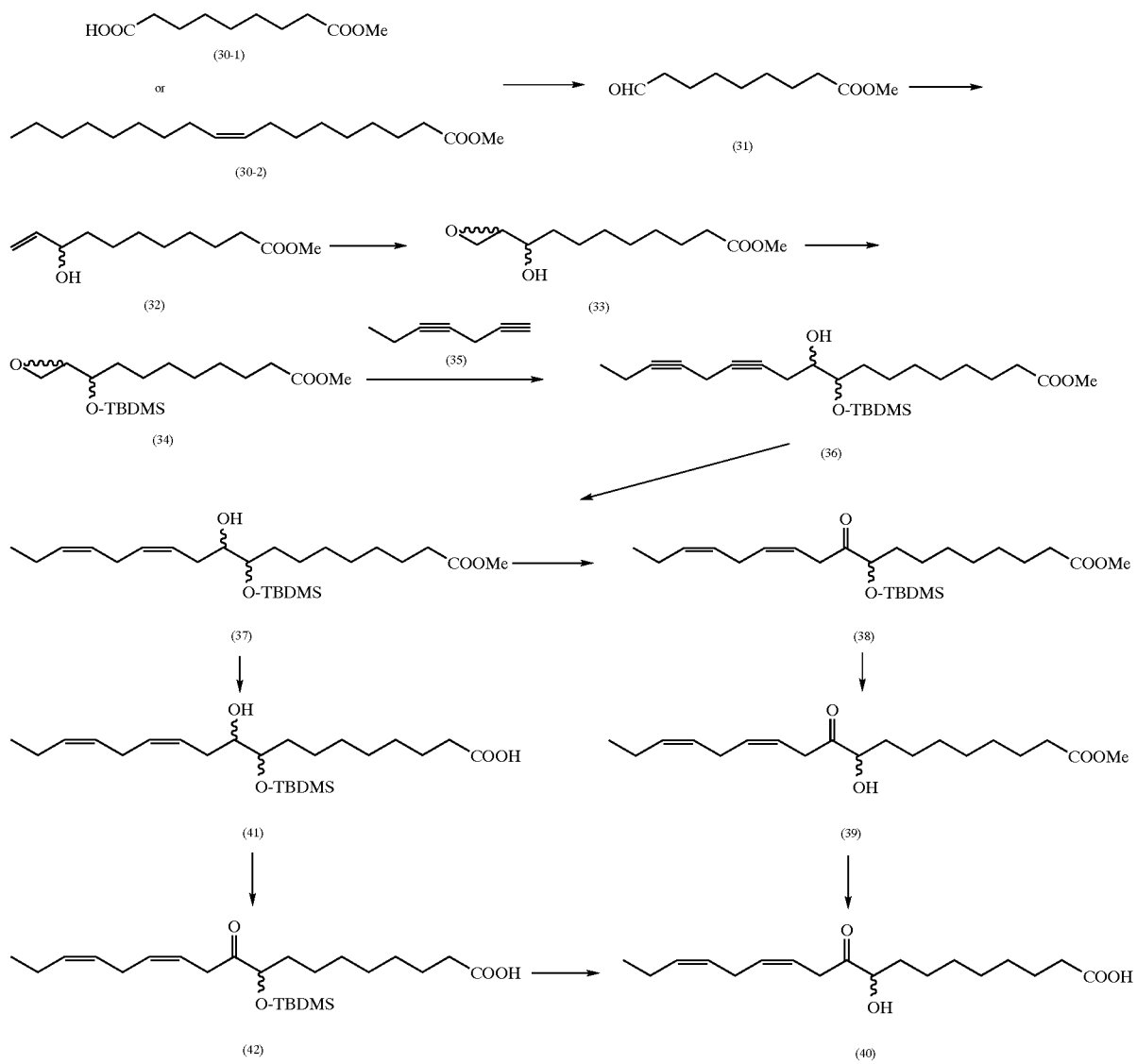

REFERENCE EXAMPLE 1

Synthesis of o-iodoxybenzoic Acid

According to a method described in J. Org. Chem., 48, 4155–4156 (1983) and Tetrahedron Lett., 35, 8019–8022 (1994), o-iodoxybenzoic acid was prepared. That is, potassium bromate (76.0 g) was gradually added into 0.73 M sulfuric acid solution (730 ml) of 2-iodobeonzoic acid (85.2 g) while being stirred strongly for 30 minutes. During this period, the temperature of the reaction mixture was kept at 55° C. or less. After being stirred for 3.6 hours at 65° C., the reaction mixture was cooled to 0° C. and then a precipitate was collected by a filtration. The precipitate was washed with water (1 litter) and ethanol (50 ml) two times, successively, to yield o-iodoxybenzoic acid (89.1 g, 93%).

Also, for synthesizing o-iodoxybenzoic acid a method described in J. Org. Chem. 64, 4537–4538 (1999) can be used.

REFERENCE EXAMPLE 2

Synthesis of Jones Regent

According to a method described in "Jikken Kagaku Koza" vol. 23, 4th Ed., edited by the Chemical Society of Japan, a Jones regent was prepared. That is, to a aqueous solution (10 ml) containing chromium oxide (VI) (7 g) was added concentrated sulfuric acid (6.1 ml) while being cooled with ice, and then water (20 ml) was further added thereto, thereby preparing Jones regent.

PREPARATION EXAMPLE 1

Synthesis of methyl 9-[(tert-butyldimethylsilyl)oxy]-9-(2-oxylanyl)nonanate (Compound 34)

(i)Methyl 9-oxononanate (Compound 31)
(Method A)

To a solution of azelaic acid monomethyl ester (4.04 g) in THF (50 ml) was added 1,1'-carbonyldiimidazole (4.86 g) and then refluxed with heating for 2 hours. After being cooled, the reaction mixture was poured into water and extracted with ethyl acetate. The organic layer was washed with saturated sodium hydrogencarbonate aqueous solution and saturated brine successively, and then dried over magnesium sulfate anhydride. The solvent was evaporated under reduced pressure to give a crude product (4.71 g).

To a solution of the crude product (4.71 g) in THF (50 ml) was dropwise added a solution of lithium aluminum hydrate tri-tert-butoxide (6.1 g) in THF (50 ml) and then stirred for 1.5 hours at room temperature. The reaction mixture which volume was reduced to about 50 ml by partial evaporation of the solvent under reduced pressure, was poured into 1N hydrochloric acid (200 ml) and then extracted with ethyl acetate. The organic layer was washed with water and saturated brine successively, and then dried over magnesium sulfate anhydride. The solvent was evaporated under reduced pressure to give methyl 9-oxononanate (3.33 g 89.3%).

(Method B)

To a solution of 70% methyl oleate (10.0 g) in dichloromethane (50 ml) was added 70% m-chloroperbenzoic acid (16.63 g) while being cooled with ice and then stirred for 1 hour at room temperature. To the reaction mixture was added saturated sodium thiosulfate aqueous solution and then extracted with diethyl ether. The organic layer was washed with saturated sodium hydrogencarbonate aqueous solution and saturated brine successively, and then dried over sodium sulfate anhydride. The solvent was evaporated under reduced pressure to give a crude product (12.73 g).

Then, to an aqueous solution (5 ml) containing periodic acid dihydrate (13.3 g) was added a solution of the resulting crude product (12.73 g) in dioxane (25 ml) and then stirred for 1 hour at room temperature. The reaction mixture was poured into water and then extracted with diethyl ether. The organic layer was washed with saturated brine, dried over sodium sulfate anhydride, and then evaporated under reduced pressure. The residue was purified by silica gel column chromatography (n-hexane:ethyl acetate=5:1) to give methyl 9-oxononanate (3.641 g, 82.8%).

(Method C)

A solution of methyl oleate (10.0 g) in methanol (100 ml) was purged of ozone with stirring at −20° C. for 1 hour. The reaction mixture, with dimethylsulfide (7.43 ml) added thereto at −20° C., was stirred for 10 minutes and then allowed to warm to room temperature. The residue obtained by evaporation of the solvent under reduced pressure was purified by silica gel column chromatography (n-hexane:ethyl acetate=5:1) to give methyl 9-oxononanate (5.65 g, 89.9%).

$^1$H-NMR(CDCl$_3$) δ: 1.22–1.59(10H), 2.28(2H, t, J=7.0 Hz), 2.40(2H, dt, J=1.5, 7.0 Hz), 3.64(3H, s), 9.74(1H, t, J=1.5 Hz).

(ii)Methyl 9-hydroxy-10-undecenate (Compound 32)

(Method A)

To a solution of methyl 9-oxononanate (260.4 mg) in THF (4 ml) was dropwise added 0.95M vinyl magnesium bromide (1.62 ml) at —70° C. and then stirred for 1 hour at −60° C. The reaction mixture was poured into a saturated ammonium chloride aqueous solution and then extracted with ethyl acetate. The organic layer was washed with saturated brine, dried over magnesium sulfate anhydride, and then evaporated under reduced pressure. The residue was purified by silica gel column chromatography (n-hexane:ethyl acetate=3:1) to give methyl 9-hydroxy-10-undecenate (144 mg, 47.4%).

(Method B)

To a solution of methyl 9-oxononanate (5.26 g) in THF (60 ml) was dropwise added 0.95M vinyl magnesium bromide (31.1 ml) at −30° C. and then stirred for 30 minutes at −25° C. The reaction mixture was poured into saturated ammonium chloride aqueous solution and then extracted with diethyl ether. The organic layer was washed with saturated brine, dried over magnesium sulfate anhydride, and then evaporated under reduced pressure. The residue was purified by silica gel column chromatography (n-hexane:ethyl acetate=3:1) to give methyl 9-hydroxy-10-undecenate (3.41 g, 56.3%).

$^1$H-NMR(CDCl$_3$) δ: 1.27–1.57(12H), 2.26(2H, t, J=7.5 Hz), 3.62(3H), 4.04(1H, m), 5.05(1H, d, J=10.0 Hz), 5.17 (1H, dd, J=1.5, 10.0 Hz), 5.82(1H, m).

(iii)Methyl 9-hydroxy-9-(2-oxylanyl)nonanate (Compound 33)

To a solution of methyl 9-hydroxy-10-undecenate (1.669 g) in dichloromethane (40 ml) was added m-chloroperbenzoic acid (3.0 g) and saturated sodium hydrogencarbonate aqueous solution (10 ml) successively. After being stirred for 6 hours at room temperature, the reaction mixture was poured into iced water and then extracted with chloroform. The organic layer was washed with saturated sodium thiosulfate aqueous solution and saturated brine successively, dried over magnesium sulfate anhydride, and then evaporated under reduced pressure. The residue was purified by silica gel column chromatography (n-hexane:ethyl acetate=3:2) to give methyl 9-hydroxy-9-(2-oxylanyl)nonanate (1.212 g, 67.6%)

$^1$H-NMR(CDCl$_3$) δ: 1.29–1.59(12H), 2.27(2H, t, J=7.5 Hz), 2.69 & 2.79(total 2H, both m), 2.94 & 2.98(total 1H, both m), 3.40 & 3.79(total 1H, both m), 3.64(3H,s).

(iv)Methyl 9-[(tert-butyldimethylsilyl)oxy]-9-(2-oxylanyl)nonanate (Compound 34)

To a solution of methyl 9-hydroxy-9-(2-oxylanyl) nonanate (1.142 g) in dimethylformamide (10 ml) was added tert-butyldimethylchlorosilane (823 mg) and imidazole (743 mg). After being stirred for 60 minutes at room temperature, the reaction mixture was poured into iced water and then extracted with ethyl acetate. The organic layer was washed with saturated sodium hydrogencarbonate aqueous solution and saturated brine successively, dried over magnesium sulfate anhydride, and then evaporated under reduced pressure. The resulting crude was purified by silica gel column chromatography (n-hexane:ethyl acetate=20:1) to give the title compound (687 mg, 40.2%).

$^1$H-NMR(CDCl$_3$) δ: 0.01(3H, s), 0.03 & 0.08(total 3H, both s), 0.85 & 0.89(total 9H, both s), 1.28–1.59(12H), 2.27(2H, t, J=7.5 Hz), 2.51 & 2.62(total 1H, dd, J=3.0, 5.0 Hz; dd, J=2.5, 5.5 Hz), 2.67 & 2.74(total 1H, dd, J=4.0, 5.5 Hz; dd, J=4.0, 4.0 Hz), 2.82 & 2.89(total 1H, both m), 3.22 & 3.52(total 1H, both m), 3.64(3H, s).

PREPARATION EXAMPLE 2

Synthesis of methyl 9-[(tert-butyldimethylsilyl) oxy]-10-hydroxy-12,15-octadecadiynate (Compound 36)

(Method A)

To a solution of 1,4-heptadiyne (17 mg) in THF (8 ml), said diyne was prepared according to a method described in Japanese Unexamined Patent Publication No.53-34926, was dropwise added 1.5M n-butyllithium solution in THF (388 μl) at −70° C. and then stirred for 1 hour at −70° C. To the reaction mixture was dropwise added a solution of methyl 9-[(tert-butyldimethylsilyl)oxy]-9-(2-oxylanyl)nonanate (85 mg) in THF (2 ml) and boron trifluoride etherate (37 μl) was further added thereto. After being stirred for 1.5 hours at −70° C., the reaction mixture with saturated ammonium chloride aqueous solution added thereto was extracted with diethyl ether. The organic layer was washed with saturated brine, dried over magnesium sulfate anhydride, and then evaporated under reduced pressure. The residue was purified by silica gel column chromatography (n-hexane:ethyl acetate=6:1) to give the title compound (93.7 mg, 87.0%)
(Method B)

To a of 1,4-heptadiyne(3.21 g) in THF (80 ml) was dropwise added 1.5M n-butyllithium solution in THF (11.61 ml) at −50° C. and then stirred for 1 hour at −50° C. To the reaction mixture was dropwise added a solution of methyl 9-[(tert-butyldimethylsilyl)oxy]-(2-oxylanyl)nonanate (3.0 g) in THF (10 ml) and then boron trifluoride etherate (1.103 ml) was further added thereto. After being stirred for 1 hour at −50° C., the reaction mixture with saturated ammonium chloride aqueous solution added thereto was extracted with diethyl ether. The organic layer was washed with saturated brine, dried over magnesium sulfate anhydride, and then evaporated under reduced pressure. The residue was purified by silica gel column chromatography (n-hexane:ethyl acetate=6:1) to give the title compound (2.43 g, 63.9%).

$^1$H-NMR(CDCl$_3$) δ: 0.05 & 0.07 & 0.08 & 0.09(total 3H×2, all s), 0.87 & 0.88(total 9H, both s), 1.09(3H, t, J=7.5 Hz), 1.08–1.60(12H), 2.14(2H, m), 2.28(2H, t, J=7.5 Hz), 2.35(2H, m), 3.10(2H, m), 3.58–3.76(2H), 3.64(3H, s).

PREPARATION EXAMPLE 3

Synthesis of 9-hydroxy-10-oxo-12(Z),15(Z)-octadecadienic Acid (Compound 40)

(i)Synthesis of methyl 9-[(tert-butyldimethylsilyl)oxy]-10-hydroxy-12(Z),15(Z)-octadecadienate (Compound 37)

To a solution of nickel acetate (II) tetrahydrate (49 mg) in methanol (2 ml) was dropwise added a solution of sodium borohydride (7.4 mg) in methanol (2 ml) while being cooled with ice and then ethylenediamine (19 μl) and methyl 9-[(tert-butyldimethylsilyl)oxy]-10-hydroxy-12,15-octadecadiynate (85 mg) were added thereto. The reaction mixture was stirred for 40 minutes in a hydrogen gas atmosphere at room temperature and then filtrated through Celite 545. The solvent was evaporated from the filtrate under reduced pressure and the residue, with saturated brine added thereto, was extracted with diethyl ether. The organic layer was washed with saturated brine, dried over magnesium sulfate anhydride, and then evaporated under reduced pressure. The residue was purified by silica gel column chromatography (n-hexane:ethyl acetate=9:1) to give methyl 9-[(tert-butyldimethylsilyl)oxy]-10-hydroxy-12(Z),15(Z)-octadecadienate (39.2 mg, 45.7%).

$^1$H-NMR(CDCl$_3$) δ: 0.03 & 0.05 & 0.06 & 0.09(total 3H x 2, all s), 0.87 & 0.88(total 9H, both s), 0.95(3H, t, J=7.5 Hz), 1.28–1.59(12H), 2.04(2H, m), 2.15 & 2.33(total 2H, both m), 2.28(2H, t, J=7.5 Hz), 2.76 & 2.88(total 2H, m), 3.45–3.75(2H), 3.64(3H, s), 5.30–5.47(4H).

(ii)Synthesis of methyl 9-[(tert-butyldimethylsilyl)oxy]-10-oxo-12(Z),15(Z)-octadecadienate (Compound 38)
(Method A)

To a solution of methyl 9-[(tert-butyldimethylsilyl)oxy]-10-hydroxy-12(Z),15(Z)-octadecadienate (20.5 mg) in dichloromethane (4 ml) was added 1M o-iodoxybenzoic acid solution in DMSO (0.1 ml) and then stirred for 2 hours at room temperature. The reaction mixture, with saturated hydrogencarbonate aqueous solution added thereto, was extracted with diethyl ether. The organic layer was washed with saturated brine, dried over magnesium sulfate anhydride, and then evaporated under reduced pressure. The residue was purified by thin-layer silica gel plate (n-hexane:ethyl acetate=9:1) to give methyl 9-[(tert-butyldimethylsilyl)oxy]-10-oxo-12(Z),15(Z)-octadecadienate (8.9 mg, 43.6%).
(Method B)

To a solution of methyl 9-[(tert-butyldimethylsilyl)oxy]-10-hydroxy-12(Z),15(Z)-octadecadienate (125 mg) in acetone (3 ml) was added Jones reagent (0.3 ml) and then stirred for 20 minutes at room temperature. The reaction mixture with saturated sodium hydrogensulfite aqueous solution added thereto was extracted with diethyl ether. The organic layer was washed with saturated hydrogencarbonate aqueous solution and saturated brine successively, dried over magnesium sulfate anhydride, and then evaporated under reduced pressure to give methyl 9-[(tert-butyldimethylsilyl)oxy]-10-oxo-12(Z),15(Z)-octadecadienate (109 mg, 87.6%).

$^1$H-NMR(CDCl$_3$) δ: 0.03(3H, s), 0.04(3H, s), 0.91(9H, s), 0.95(3H, t, J=7.5 Hz), 1.26–1.56(12H), 2.04(2H, m), 2.27 (2H, t, J=7.5 Hz), 2.74(2H, t, J=6.0 Hz), 3.34(2H, dd, J=5.0, 7.0 Hz), 3.64(3H, s), 4.03(1H, dd, J=5.5, 7.5 Hz), 5.28(1H, m), 5.38(1H, m), 5.56(2H, m).

(iii) Methyl 9-hydroxy-10-oxo-12(Z),15(Z)-octadecadienate (Compound 39)
(Method A)

Methyl 9-[(tert-butyldimethylsilyl)oxy]-10-oxo-12(Z),15 (Z)-octadecadienate (2.5 mg) was dissolved in a mixed solution (0.5 ml) of 46% hydrogen fluoride aqueous solution:acetonitrile=1:19 and then stirred for 30 minutes at room temperature. The reaction mixture with saturated hydrogencarbonate aqueous solution, was extracted with diethyl ether. The organic layer was washed with saturated brine, dried over magnesium sulfate anhydride, and then evaporated under reduced pressure. The residue was purified by thin-layer silica gel plate (n-hexane:ethyl acetate=4:1) to give methyl 9-hydroxy-10-oxo-12(Z),15(Z)-octadecadienate (2.0 mg, 100%).
(Method B)

To a solution of methyl 9-[(tert-butyldimethylsilyl)oxy]-10-oxo-12(Z),15(Z)-octadecadienate (42 mg) in acetonitrile (1 ml) was added boron trifluoride etherate (150 μl) while being cooled with ice and then stirred for 3 hours. The reaction mixture with saturated hydrogencarbonate aqueous solution added thereto was extracted with ethyl acetate. The organic layer was washed with saturated sodium hydrogen-carbonate aqueous solution and saturated brine successively, dried over magnesium sulfate anhydride, and then evaporated under reduced pressure. The residue was purified by thin-layer silica gel plate (n-hexane:ethyl acetate=4:1) to give methyl 9-hydroxy-10-oxo-12(Z),15(Z)-octadecadienate (23 mg, 75.8%).

$^1$H-NMR(CDCl$_3$) δ: 0.96(3H, t, J=7.5 Hz), 1.23–1.80 (12H), 2.04(2H, m), 2.28(2H, t, J=7.5 Hz), 2.76(2H, t, J=7.5 Hz), 3.25(2H, t, J=8.0 Hz), 3.36(1H, d J=5.0 Hz), 3.64(3H, s), 4.21(1H, m), 5.26(1H, m), 5.41(1H, m), 5.54(1H, m), 5.60(1H, m).

(iv) 9-Hydroxy-10-oxo-12(Z),15(Z)-octadecadienic Acid (Compound 40)
(Method A)

Methyl 9-hydroxy-10-oxo-12(Z),15(Z)-octadecadienate (1.0 mg) and Tween 80 (1.0 mg) were dissolved in 40 mM phosphate buffer pH 7.0 (0.5 ml). The solution, with lipase (Sigma XIV, Sigma Chemical Co.) (3.0 mg) added thereto, was placed for 24 hours at 37° C. The reaction mixture was purified by high-performance liquid chromatography (ODS column, acetonitrile:water=1:1 including 0.01% TFA) to give the title compound (0.6 mg, 60%).

(Method B)

Methyl 9-hydroxy-10-oxo-12(Z),15(Z)-octadecadienate (12 mg) was dissolved in a mixed solution (1 ml) of 0.1M phosphate buffer pH 7.0:acetone=9:1. The solution, with Lipase PS (AMANO SEIYAKU Co., Ltd.) (12 mg) added thereto, was stirred for 30 minutes at room temperature. The reaction mixture was poured into water and extracted with ethyl acetate. The organic layer was washed with saturated brine, dried over sodium sulfate anhydride, and then evaporated under reduced pressure to give the title compound (5.8 mg, 50.5%).

$^1$H-NMR(CD$_3$OD) δ: 0.97(3H, t, J=7.5 Hz), 1.28–1.71 (12H), 2.08(2H, m), 2.26(2H, t, J=7.5 Hz), 2.79(2H, m), 3.35(2H, t, J=5.0 Hz), 4.10(1H, m), 5.29(1H, m), 5.40(1H, m), 5.54(2H, m).

PREPARATION EXAMPLE 4

Synthesis of 9-hydroxy-10-oxo-12(Z),15(Z)-octadecadienic Acid (Compound 40)

(i) 9-[(tert-Butyldimethylsilyl)oxy]-10-hydroxy-12(Z),15(Z)-octadecadienic Acid (Compound 41)

Methyl 9-[(tert-butyldimethylsilyl)oxy]-10-hydroxy-12(Z),15(Z)-octadecadienate (16.0 mg) obtained in Preparation Example 3 (i) was dissolved in a mixed solution (1 ml) of 5% potassium hydroxide solution in methanol:water=3:1 and stirred for 45 minutes at room temperature. The reaction mixture was neutralized with 1N hydrochloric acid, and then extracted with diethyl ether. The organic layer was washed with saturated brine, dried over magnesium sulfate anhydride, and then evaporated under reduced pressure. The residue was purified by thin-layer silica gel plate (n-hexane:acetone=2:1) to give 9-[(tert-butyldimethylsilyl)oxy]-10-hydroxy-12(Z),15(Z)-octadecadienic acid (15.1 mg, 100%).

$^1$H-NMR(CDCl$_3$) δ: 0.08(3H), 0.09 & 0.10(total 3H, both s), 0.91 & 0.92(total 9H, both s), 0.98(3H, t, J=7.5 Hz), 1.27–1.65(12H), 2.07(2H, m), 2.18–2.34(2H), 2.36(2H, t, J=7.5 Hz), 2.81 & 2.91(total 2H, both m), 3.42–3.76(2H), 5.35–5.49(4H).

(ii) Synthesis of 9-[(tert-butyldimethylsilyl)oxy]-10-oxo-12(Z),15(Z)-octadecadienic Acid (Compound 42)

To a solution of 9-[(tert-butyldimethylsilyl)oxy]-10-hydroxy-12(Z),15(Z)-octadecadienic acid (15.1 mg) in dichloromethane (1 ml) was added 1M o-iodoxybenzoic acid in DMSO (0.1 ml) and stirred for 1 hour at room temperature. The reaction mixture, with water added thereto, was extracted with diethyl ether. The organic layer was washed with saturated brine, dried over magnesium sulfate anhydride, and then evaporated under reduced pressure. The residue was purified by thin-layer silica gel plate (n-hexane:ethyl acetate=2:1) to give 9-[(tert-butyldimethylsilyl)oxy]-10-oxo-12(Z),15(Z)-octadecadienic acid (6.8 mg, 45.2%).

$^1$H-NMR(CDCl$_3$) δ: 0.03(3H, s), 0.04(3H, s), 0.91(9H, s), 0.95(3H, t, J=7.5 Hz), 1.24–1.61(12H), 2.04(2H, m), 2.32 (2H, t, J=7.5 Hz), 2.74(2H, m), 3.34(2H, t, J=5.0 Hz), 4.03(1H, m), 5.28(1H, m), 5.39(1H, m), 5.56(2H, m).

(iii) 9-Hydroxy-10-oxo-12(Z),15(Z)-octadecadienic Acid (Compound 40)

9-[(tert-Butyldimethylsilyl)oxy]-10-oxo-12(Z),15(Z)-octadecadienic acid (3.4 mg) was dissolved in a mixed solution (0.5 ml) of 46% hydrogen fluoride aqueous solution:acetonitrile=1:19 and then stirred for 30 minutes at room temperature. The reaction mixture, with water added thereto, was extracted with diethyl ether. The organic layer was washed with saturated brine ten times, dried over magnesium sulfate anhydride, and then evaporated under reduced pressure. The residue was purified by thin-layer silica gel plate (n-hexane:ethyl acetate=1:1) to give the title compound (1.5 mg, 60.4%).

In addition, as a typical example of an optically active α-ketol unsaturated fatty acid, a synthetic example of (R)-9-hydroxy-10-oxo-12(Z),15(Z)-octadecadienic acid (Compound 40A) will be described in below. The $^1$H-NMR data of each compounds is same as that of the corresponding racemate. With respect to compound 32A, it was verified by New Mosher method that its 9-position had R-configuration. Also, since an optical rotation of compound 40A which was finally product was same as an authentic sample, it was verified that 9-position of each compounds had R-configuration.

Reaction Formula 6

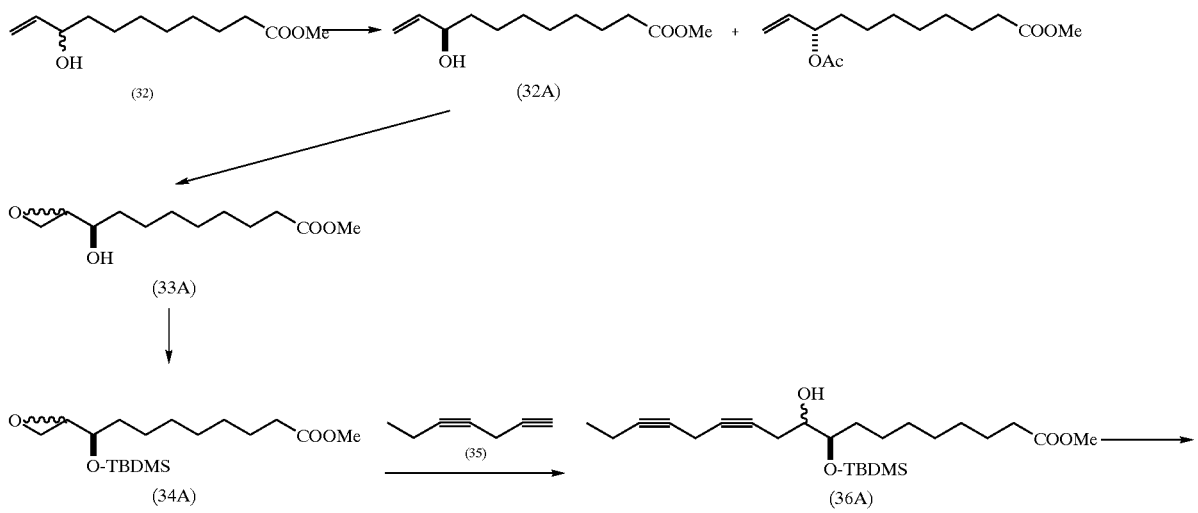

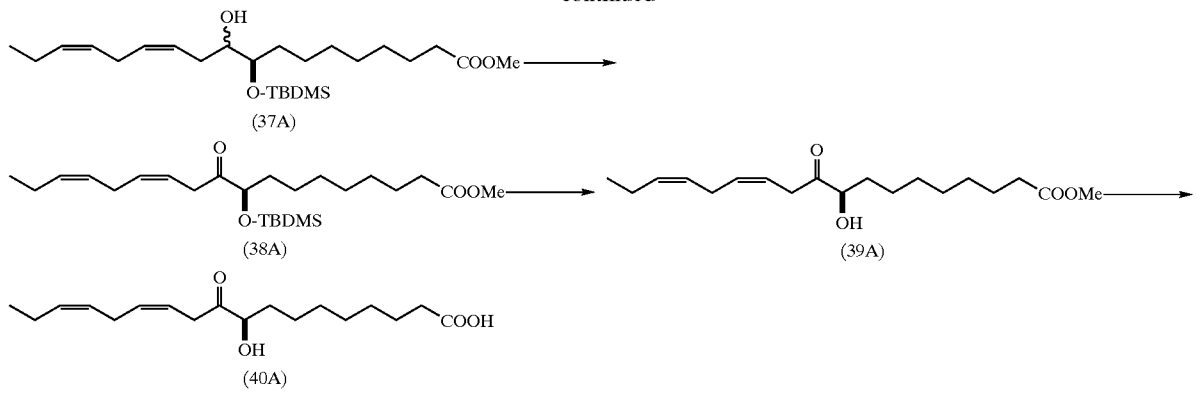

PREPARATION EXAMPLE 5

Synthesis of (R)-9-hydroxy-10-oxo-12(Z),15(Z)-octadecadienic Acid (Compound 40A)

(i)(R)-Methyl 9-hydroxy-10-undecenate (Compound 32A)

(Method A)

To a solution of methyl 9-hydroxy-10-undecenate (500 mg) in diisopropyl ether (12 ml) was added vinyl acetate (323 μl) and Lipase PS (AMANO SEIYAKU Co., Ltd.) (500 mg) and then shaken for 62 hours at 30° C. The reaction mixture was filtrated and the filtrate was poured into ethyl acetate. The organic layer was washed with saturated brine, dried over magnesium sulfate anhydride, and then evaporated under reduced pressure. The resulting product was purified by silica gel column chromatography (n-hexane:ethyl acetate=3:1) to give (R)-methyl 9-hydroxy-10-undecenate (152 mg, 30.4%).

(Method B)

To a solution of methyl 9-hydroxy-10-undecenate (509 mg) in pentane (12 ml) was added vinyl acetate (1.097 ml) and Lipase PS (AMANO SEIYAKU Co., Ltd.) (238 mg) and then shaken for 62 hours at 30° C. The reaction mixture was filtrated and the filtrate was poured into ethyl acetate, washed with saturated brine, dried over magnesium sulfate anhydride, and then evaporated under reduced pressure. The resulting product was purified by silica gel column chromatography (n-hexane:ethyl acetate=3:1) to give (R)-methyl 9-hydroxy-10-undecenate (168 mg, 33.6%).

(Method C)

To a solution of methyl 9-hydroxy-10-undecenate (9.38 g) in pentane (150 ml) was added vinyl acetate (4.037 ml) and Lipase PS (AMANO SEIYAKU Co., Ltd.) (2.190 g) and then shaken at 30° C. After 48 hours, the reaction was stopped and the reaction mixture was filtrated. The filtrate was poured into ethyl acetate, washed with saturated brine, dried over magnesium sulfate anhydride, and then evaporated under reduced pressure. The resulting product was purified by silica gel column chromatography (n-hexane:ethyl acetate=5:2) to give methyl 9-hydroxy-10-undecenate (5.999 g, 64.0%) as a mixture of R-isomer:S-isomer=2:1. When the reaction is stopped halfway like this case, it is possible to control a ratio between R- and S-isomer freely.

(Method D)

To a solution of methyl 9-hydroxy-10-undecenate (5.293 g) in pentane (100 ml) was added vinyl acetate (11.38 ml) and Lipase PS (AMANO SEIYAKU Co., Ltd.) (1.235 g) and then shaken for 72 hours at 30° C. The reaction mixture was filtrated and the filtrate was poured into ethyl acetate, washed with saturated brine, dried over magnesium sulfate anhydride, and then evaporated under reduced pressure. The resulting product was purified by silica gel column chromatography (n-hexane:ethyl acetate=5:2) to give (R)-methyl 9-hydroxy-10-undecenate (1.937 g, 36.7%).

Determination of Compound 32A's Configuration by New Mosher Method

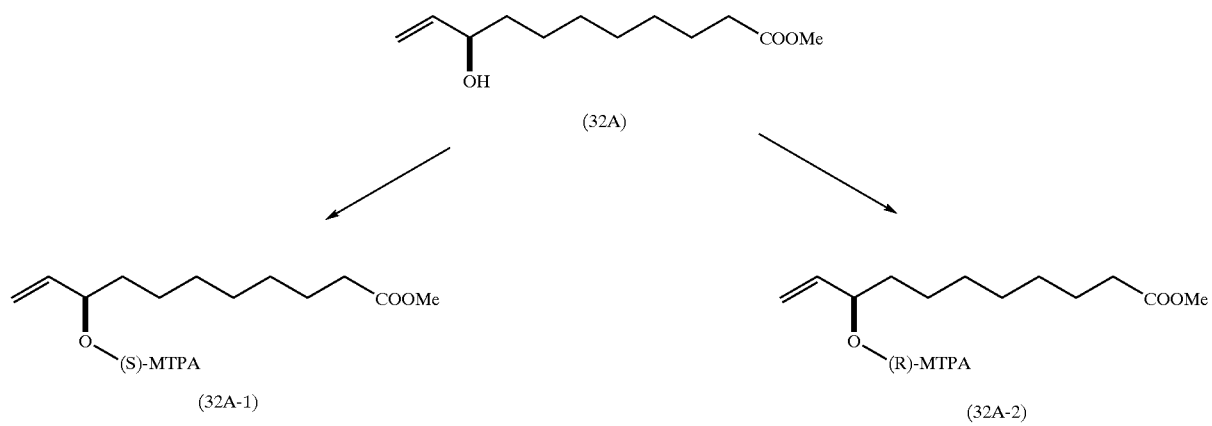

(1) Synthesis of (S)-MTPA ester(32A-1) of Compound 32A

To a solution of (S)-2-methoxy-2-trifluoromethylphenylacetic acid ((S)-MTPA) (15 mg) in dichloromethane (1 ml) was added 1-ethyl-3-(3-dimethylaminopropyl)carbodiimide hydrochloride (15 ml), 4-dimethylaminopyridine (10 mg) and compound 32A (5 mg) and then stirred for 5 hours at room temperature. The reaction mixture was poured into water and then extracted with ethyl acetate. The organic layer was washed with 5% hydrochloric acid, saturated hydrogencarbonate aqueous solution, and saturated brine successively, dried over magnesium sulfate anhydride, and then evaporated under reduced pressure. The residue was purified by thin-layer silica gel plate (n-hexane:ethyl acetate=4:1) to give compound 32A-1 (4 mg, 39.8%).

$^1$H-NMR(CDCl$_3$) δ: 1.26–1.72 (12H), 2.2941 (2H, t, J=7.5 Hz, 2-H), 3.55 (3H), 3.66 (3H), 5.19 (1H, d-like, J=10.5 Hz), 5.25 (1H, d-like, J=17.5 Hz), 5.43 (1H, m), 5.7205 (1H, m, 10-H), 7.38–7.52 (5H).

(2) Synthesis of (R)-MTPA ester(32A-2) of Compound 32A

Using (R)-2-methoxy-2-trifluoromethylacetic acid(i.e., (R)-MTPA), in a same manner to compound 32A-1, compound 32A-2 was prepared.

$^1$H-NMR(CDCl$_3$) δ: 1.23–1.70 (12H), 2.2867 (2H, t, J=7.5 Hz, 2-H), 3.55 (3H), 3.66 (3H), 5.25 (1H, dd, J=1.0, 10.5 Hz), 5.35 (1H, dd, J=1.0, 17.5 Hz), 5.45 (1H, m), 5.8167 (1H, m, 10-H), 7.37–7.53 (5H).

(3) Determination of 9-Configuration of Compound 32A

It is known that the configuration of secondary hydroxyl group can be determined by application of New Mosher Method (Journal of American Chemical Society, 113, 4092 (1991)).

As a result in application of this method to compound 32A, Δδ volumes were −0.0962 and +0.0074 at 10- and 2-position respectively. The Δδ volume was calculated by using $^1$H-NMR data of each MTPA esters of compound 32A (i.e., compound 32A-1 and 32A-2) according to the following equation:

Δδ=δ(Compound 32A-1)−δ(Compound 32A-2).

Due to this, it could be verified that 9-position of compound 32A had R-configuration.

(ii) Synthesis of (R)-methyl 9-hydroxy-9-(2-oxylanyl) nonanate (Compound 33A)

To a solution of (R)-methyl 9-hydroxy-10-undecenate (6.81 g) in dichloromethane (90 ml) was added m-chloroperbenzoic acid (70% purity, including moisture, manufactured by WAKO PURE CHEMICAL INDUSTRIES Ltd.) (15.67 g) and then stirred for 2 hours at room temperature. To the reaction mixture concentrated to about 30 ml by removing the solvent under reduced pressure was dropwise added saturated sodium thiosulfate aqueous solution while being cooled with ice. This mixture was extracted with diethyl ether and the extract was washed with saturated hydrogencarbonate aqueous solution and saturated brine successively, dried over magnesium sulfate anhydride, and then evaporated under reduced pressure to give (R)-methyl 9-hydroxy-9-(2-oxylanyl) nonanate (7.414 g, 100%).

(iii) Synthesis of (R)-methyl 9-[(tert-butyldimethylsilyl) oxy]-9-(2-oxylanyl) nonanate (Compound 34A)
(Method A)

To a solution of (R)-methyl 9-hydroxy-9-(2-oxylanyl) nonanate (166 mg) in dimethylformamide (3 ml) was added tert-butyldimethylchlorosilane (217 mg) and imidazole (196 mg), and then stirred for 18 hours at room temperature. The reaction mixture was poured into iced water and then extracted with ethyl acetate. The organic layer was washed with saturated sodium hydrogencarbonate aqueous solution and saturated brine successively, dried over magnesium sulfate anhydride, and then evaporated under reduced pressure. The crude resultant was purified by silica gel column chromatography (n-hexane:ethyl acetate=10:1) to give (R)-methyl 9-[(tert-butyldimethylsilyl)oxy]-9-(2-oxylanyl) nonanate (185.1 mg, 74.5%).
(Method B)

To a solution of (R)-methyl 9-hydroxy-9-(2-oxylanyl) nonanate (7.414 g) in dimethylformamide (70 ml) was added tert-butyldimethylchlorosilane (9.65 g) and imidazole (8.77 g), and then stirred for 18 hours at room temperature. The reaction mixture concentrated to about 30 ml by removing the solvent under reduced pressure was poured into iced water and extracted with ethyl acetate. The organic layer was washed with 5% hydrochloric acid, saturated sodium hydrogencarbonate aqueous solution and saturated brine successively, dried over magnesium sulfate anhydride, and then evaporated under reduced pressure. The crude resultant was purified by silica gel column chromatography (n-hexane:ethyl acetate=10:1) to give (R)-methyl 9-[(tert-butyldimethylsilyl)oxy]-9-(2-oxylanyl)nonanate (2.994 g, 27.0%).

(iv) Synthesis of (R)-methyl 9-[(tert-butyldimethylsilyl) oxy]-10-hydroxy-12,15-octadecadiynate (Compound 36A)

To a solution of 1,4-heptadiyne (3.14 g) in THF (20 ml) was dropwise added 1.5M n-butyllithium solution in THF (10.7 ml) at −70° C. and then stirred for 45 minutes at −70° C. To the reaction mixture was dropwise added a solution of (R)-methyl 9-[(tert-butyldimethylsilyl)oxy]-9-(2-oxylanyl) nonanate (2.83 g) in THF (5 ml) and further added boron trifluoride etherate (1.19 ml). After being stirred for an additional 1 hour at −70° C., the reaction mixture with saturated ammonium chloride aqueous solution added thereto was extracted with diethyl ether. The extract was washed with saturated brine, dried over magnesium sulfate anhydride, and then evaporated under reduced pressure, to give (R)-methyl 9-[(tert-butyldimethylsilyl)oxy]-10-hydroxy-12,15-octadecadiynate (4.18 g, 100%).

(v) Synthesis of (R)-methyl 9-[(tert-butyldimethylsilyl) oxy]-10-hydroxy-12(Z),15(Z)-octadecadienate (Compound 37A)

To a solution of (R)-methyl 9-[(tert-butyldimethylsilyl) oxy]-10-hydroxy-12,15-octadecadiynate (3.96 g) in toluene (30 ml) was added Lindlar catalyst (palladium, 5 wt % on CaCO$_3$, poisoned with lead) (200 mg) and stirred for 1 hour at room temperature in a hydrogen gas atmosphere. The reaction mixture was filtrated through Celite 545 and the filtrate with saturated brine added thereto was extracted with ethyl acetate. The organic layer was washed with saturated brine, dried over magnesium sulfate anhydride, and then evaporated under reduced pressure. The crude resultant was purified by silica gel column chromatography (n-hexane:ethyl acetate=9:1) to give (R)-methyl 9-[(tert-butyldimethylsilyl)oxy]-10-hydroxy-12(Z),15(Z)-octadecadienate (2.427 g, 60.7%).

(vi) Synthesis of (R)-methyl 9-[(tert-butyldimethylsilyl) oxy]-10-oxo-12(Z),15(Z)-octadecadienate (Compound 38A)

To a solution of (R)-methyl 9-[(tert-butyldimethylsilyl) oxy]-10-hydroxy-12(Z),15(Z)-octadecadienate (2.312 g) in acetone (20 ml) was added dropwise slowly Jones regent (5.0 ml) while being cooled with ice and stirred for 40 minutes at room temperature. The reaction mixture with saturated sodium hydrogensulfite aqueous solution added thereto was extracted with diethyl ether. The organic layer was washed with saturated hydrogencarbonate aqueous solution and saturated brine successively, dried over magnesium sulfate anhydride, and then evaporated under reduced pressure to give (R)-methyl 9-[(tert-butyldimethylsilyl)oxy]-10-oxo-12(Z),15(Z)-octadecadienate (2.222 g, 96.5%).

(vii) Synthesis of (R)-methyl 9-hydroxy-10-oxo-12(Z),15(Z)-octadecadienate (Compound 39A)

To a solution of (R)-methyl 9-[(tert-butyldimethylsilyl)oxy]-10-oxo-12(Z),15(Z)-octadecadienate (2.20 g) in acetonitryl (20 ml) was added boron trifluoride etherate (539 µl) while being cooled with ice and then stirred for 35 minutes under the same cooled condition. The reaction mixture with saturated hydrogencarbonate aqueous solution added thereto was extracted with diethyl ether. The organic layer was washed with saturated hydrogencarbonate aqueous solution and saturated brine successively, dried over magnesium sulfate anhydride, and then evaporated under reduced pressure. The residue was purified by silica gel column chromatography (n-hexane:ethyl acetate=4:1) to give (R)-methyl 9-hydroxy-10-oxo-12(Z),15(Z)-octadecadienate (447.4 mg, 27.5%).

(viii) Synthesis of (R)-9-hydroxy-10-oxo-12(Z),15(Z)-octadecadienic Acid (Compound 40A)

(R)-Methyl 9-hydroxy-10-oxo-12(Z),15(Z)-octadecadienate (387.4 mg) was dissolved in a mixed solution (6 ml) of 0.1M phosphate buffer (pH 7.0):acetone=1:1. To the solution was added Lipase PS (AMANO SEIYAKU Co., Ltd.) (40 mg) and stirred for 15 hours at room temperature. The reaction mixture was poured into water and extracted with ethyl acetate. The organic layer was washed with saturated brine, dried over sodium sulfate anhydride, and then evaporated under reduced pressure to give the title compound (373.8 mg, 100%).

Comparative Example 1

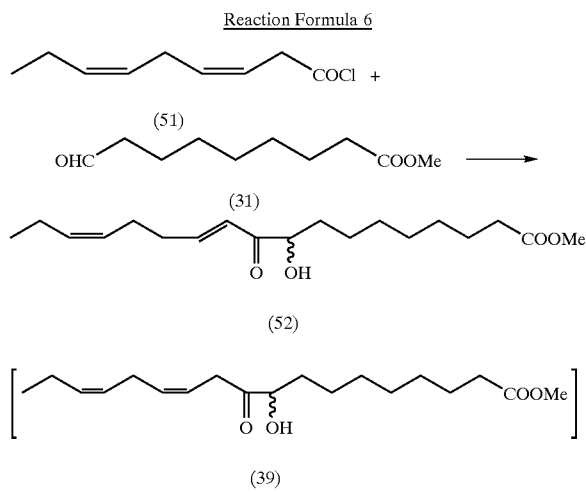

Reaction Formula 6

To a solution of samarium diiodide (40 mg) in acetonitrile (1 ml) was added a solution of compound (31) (60 mg) in acetonitrile (1 ml) and further added a solution of compound (51) (40 mg) in acetonitrile (2 ml). After stirring for 20 minutes at room temperature, the reaction mixture with 1N hydrochloric acid (10 ml) added thereto was extracted with diethyl ether. The organic layer was washed with 10% sodium thiosulfate aqueous solution, dried over magnesium sulfate anhydride, and then evaporated under reduced pressure. The residue was purified by silica gel column chromatography (n-hexane:ethyl acetate=5:1) to give compound (52) (13.2 mg, 17.6%), but the aimed Compound 39 could not be isolated.

$^1$H-NMR(CDCl$_3$) δ: 0.97(3H, t, J=7.5 Hz), 1.25–1.79 (14H), 2.05(2H, m), 2.30(2H, t, J=7.5 Hz), 2.41(2H, m), 3.64(3H, s), 4.34(1H, m), 5.29(1H, m), 5.43(1H, m), 6.24 (1H d, J=16.0 Hz), 7.03(1H, dt, J=16.0, 6.5 Hz).

Comparative Example 2

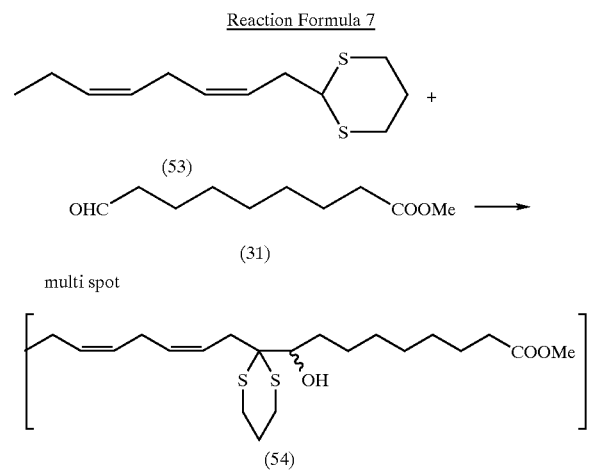

Reaction Formula 7

To a solution of compound (53) (110 mg) in THF (4 ml) was added hexamethylphosphoramido (HMPA) (10 mg). After being cooled to −60° C., the mixture with 1.5M n-butyllithium solution in THF (386 µl) dropwise added thereto was stirred at −20° C. for 30 minutes. To the reaction mixture was dropwise added a solution of compound (31) (179 mg) in THF (5 ml) and then stirred for 15 minutes at −20° C. The reaction mixture with saturated ammonium chloride aqueous solution was extracted with diethyl ether. The organic layer was washed with saturated brine, dried over magnesium sulfate anhydride, and then evaporated under reduced pressure. The resultant was a complicated mixture and the aimed compound (54) could not be isolated.

Comparative Example 3

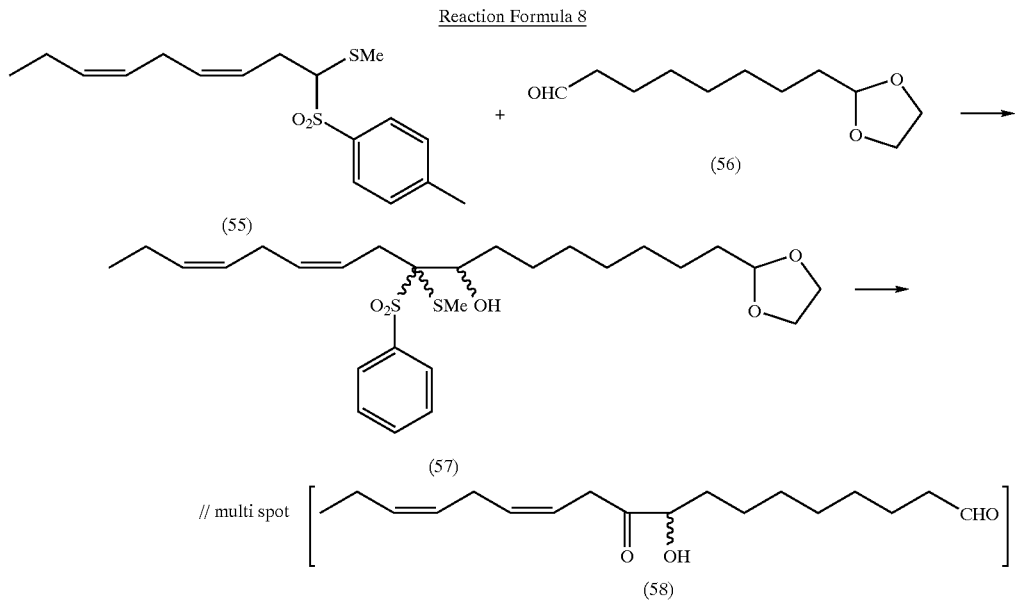

Reaction Formula 8

To a solution of compound (55) (53.7 mg) in THF (3.5 ml) was added 1.5M n-butyllithium solution in THF (133 µl) dropwise added thereto and stirred for 1 hour at a temperature in the range of −60° C. to −30° C. To the reaction mixture was dropwise added a solution of Compound 56 (49.8 mg) in THF (3 ml) at −30° C. and then stirred at −30° C. for 1 hour. The reaction mixture with saturated ammonium chloride aqueous solution was extracted with diethyl ether. The organic layer was washed with saturated brine, dried over magnesium sulfate anhydride, and then evaporated under reduced pressure. The residue was purified by silica gel column chromatography (n-hexane:ethyl acetate= 3:1) to give compound (57) (13.5 mg, 15.5%).

$^1$H-NMR(CDCl$_3$) δ: 0.95(3H, t, J=7.5 Hz), 1.30–1.60 (14H), 2.02(2H, m), 2.38(3H, s), 2.39(2H, m), 2.44(3H, s), 2.72 & 2.77(total 2H, both m), 3.82(2H, m), 3.92(2H, m), 4.05 & 4.14(total 1H, m), 4.81(1H, t, J=4.5 Hz), 5.25(1H, m), 5.37(2H, m), 5.48(1H, m), 7.33(2H, d, J=8.0 Hz), 7.84(2H, d, J=8.0 Hz).

Compound (57) (3.8 mg) was dissolved in a mixed solution (1 ml) of concentrated hydrochloric acid:methanol= 7:100 and refluxed for 1 hour with heating. The reaction mixture was neutralized through ion exchange resin (Amberlite IRA-68, OH$^+$ form) and the solvent was evaporated under reduced pressure. The resultant was a complicated mixture and the aimed compound (58) could not be isolated.

As described in the foregoing, by the synthetic method of the present invention α-ketol unsaturated fatty acid wherein a double bond exists at β-position to a ketone group can be efficiently prepared, thereby improving the yield thereof.

We claim:

1. A method of synthesizing an α-ketol unsaturated fatty acid comprising the steps of:

preparing compound (4) by reacting monosubstituted acetylene (2) with epoxide (3); and preparing α-ketol unsaturated fatty acid (1) from said compound (4), as shown in Reaction Formula 1:

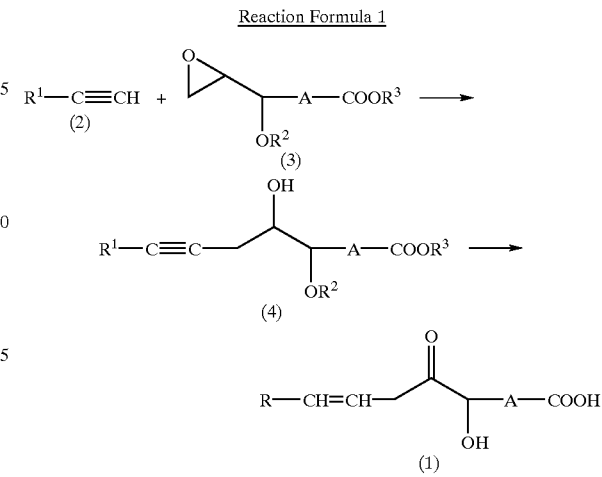

Reaction Formula 1 wherein $R^1$ represents an alkyl group of 1–18 carbon atoms or an aliphatic hydrocarbon group of 2–18 carbon atoms having 1–5 double or triple bonds at given positions;

$R^2$ represents a protecting group for a hydroxyl group;

$R^3$ represents a protecting group for a carboxyl group;

R is identical to $R^1$ or, when $R^1$ has one or more triple bonds, R represents an aliphatic hydrocarbon group in which each triple bond of $R^1$ is converted to a double bond; and A represents an alkylene group of 1–18 carbon atoms.

2. The method according to claim 1 comprising the steps of:

reducing said compound (4) to produce compound (5);

oxidizing a hydroxyl group of said compound (5) to produce compound (6); and deprotecting $R^2$ and $R^3$ of said compound (6) to produce said α-ketol unsaturated fatty acid (1), as shown in Reaction Formula 2:

Reaction Formula 2

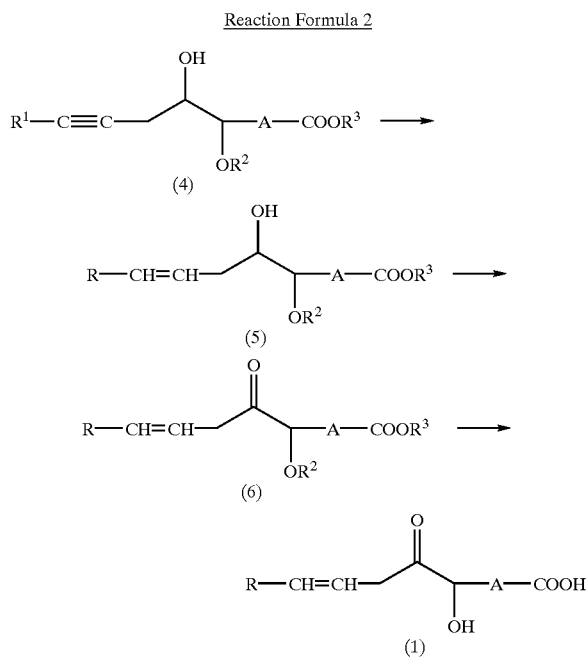

wherein $R^1$, $R^2$, $R^3$, R, and A are the same as defined in said Reaction Formula 1.

3. The method according to claim 1 comprising the steps of:

reducing said compound (4) to produce compound (5);

deprotecting $R^3$ of said compound (5) to produce compound (7);

oxidizing a hydroxyl group of said compound (7) to produce compound (8); and deprotecting $R^2$ of said compound (8) to produce said α-ketol unsaturated fatty acid (1), as shown in Reaction Formula 3:

Reaction Formula 3

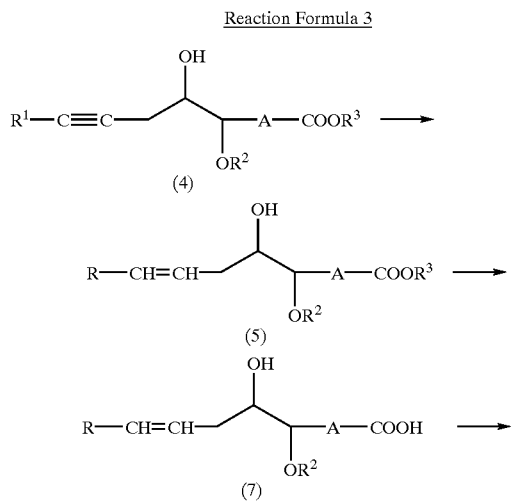

-continued

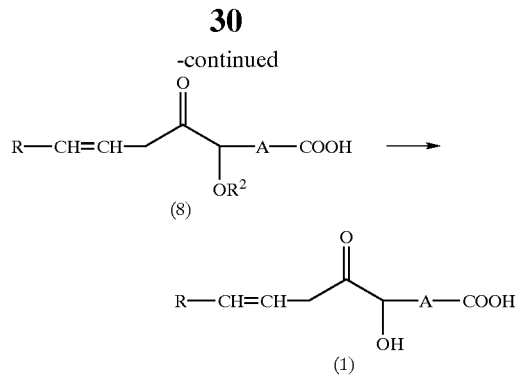

wherein $R^1$, $R^2$, $R^3$, R, and A are the same as defined in said Reaction Formula 1.

4. The method according to claim 1, wherein $R^1$ represents
$R^4$—C≡C—$CH_2$—; wherein $R^4$ represents an alkyl group of 1–7 carbon atoms.

5. The method according to claim 4, wherein $R^4$ represents ethyl group.

6. The method according to claim 1, wherein A represents an alkylene group expressed by —$(CH_2)_n$—; wherein n is an integer of 1 to 10.

7. The method according to claim 6, wherein n is equal to 7.

8. The method according to claim 1, wherein $R^2$ represents an ether-type protecting group.

9. The method according to claim 1, wherein the double bond of the α-ketol unsaturated fatty acid (1) has a cis-configuration.

10. An intermediate for synthesis of a-ketol unsaturated fatty acid (1) as described in claim 1, represented by the general formula (4):

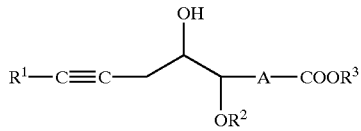

wherein $R^1$ represents an alkyl group of 1–18 carbon atoms or an aliphatic hydrocarbon group of 2–18 carbon atoms having 1–5 double or triple bonds at given positions;

$R^2$ represents a protecting group for a hydroxyl group;

$R^3$ represents a protecting group for a carboxyl group; and

A represents an alkylene group of 1–18 carbon atoms.

11. The method according to claim 1, which is a method of synthesizing an optically active α-ketol unsaturated fatty acid, wherein an asymmetric carbon atom of —C($OR^2$)— in said epoxide (3) has either of R-configuration or S-configuration, and an asymmetric carbon atom in the α-ketol structure of said α-ketol unsaturated fatty acid (1) has either of R-configuration or S-configuration.

12. The method according to claim 11 comprising the steps of:

preparing compound (4A) by reacting said monosubstituted acetylene (2) with (R)-epoxide (3A) obtained from compound (21A) which asymmetric carbon atom at an aryl position has R-configuration; and preparing (R)-α-ketol unsaturated fatty acid (1A) from said compound (4A), as shown in Reaction Formula 1A:

Reaction Formula 1A

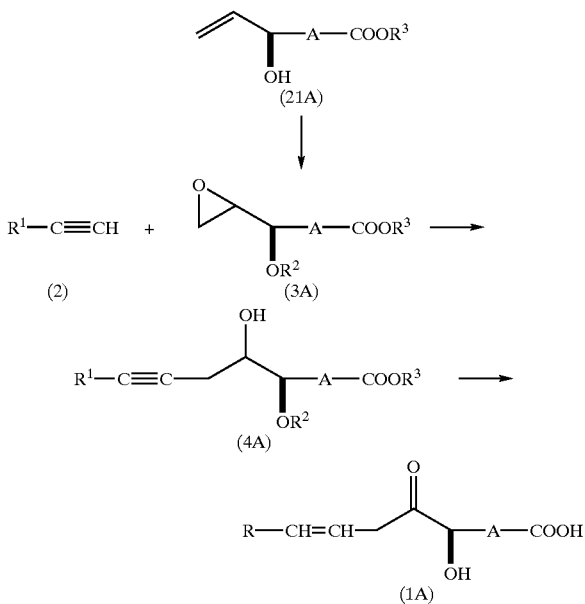

wherein $R^1$, $R^2$, $R^3$, R, and A are the same as defined in said Reaction Formula 1.

13. The method according to claim 11 comprising the steps of:

preparing compound (4B) by reacting said monosubstituted acetylene (2) with (S)-epoxide (3B) obtained from compound (21B) which asymmetric carbon atom at an aryl position has S-configuration; and preparing (S)-α-ketol unsaturated fatty acid (1B) from said compound (4B), as shown in Reaction Formula 1B:

Reaction Formula 1B

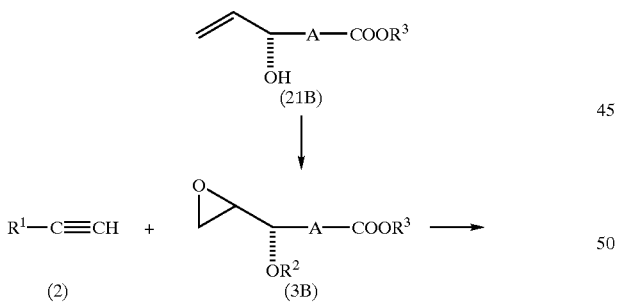

wherein $R^1$, $R^2$, $R^3$, R, and A are the same as defined in said Reaction Formula 1.

14. An optically active intermediate for synthesis of α-ketol unsaturated fatty acid (1A) or (1B) as described in claim 11, represented by the general formula (4A) or (4B):

wherein $R^1$ represents an alkyl group of 1–18 carbon atoms or an aliphatic hydrocarbon group of 2–18 carbon atoms having 1–5 double or triple bonds at given positions;

$R^2$ represents a protecting group for a hydroxyl group;

$R^3$ represents a protecting group for a carboxyl group; and

A represents an alkylene group of 1–18 carbon atoms.

* * * * *